(12) United States Patent
Unhoch

(10) Patent No.: US 7,122,505 B1  
(45) Date of Patent: Oct. 17, 2006

(54) COMPOSITION FOR CONTROLLING THE GROWTH OF ALGAE, FUNGI AND PATHOGENIC ORGANISMS IN WATER

(75) Inventor: Michael J Unhoch, Wilmington, DE (US)

(73) Assignee: Arch Chemicals Inc., Norwalk, CT (US)

( * ) Notice: Subject to any disclaimer, the term of this patent is extended or adjusted under 35 U.S.C. 154(b) by 0 days.

(21) Appl. No.: 09/422,231

(22) Filed: Oct. 21, 1999

(51) Int. Cl.  
*A01N 25/32* (2006.01)  
*A01N 33/12* (2006.01)  
*A01N 47/44* (2006.01)

(52) U.S. Cl. ............ 504/151; 504/153; 504/158; 504/159; 424/613

(58) Field of Classification Search ........... 564/233; 424/405, 613; 514/483, 480; 504/151, 153, 504/158, 159  
See application file for complete search history.

(56) References Cited

U.S. PATENT DOCUMENTS

| | | | |
|---|---|---|---|
| 4,014,676 A * | 3/1977 | Carter et al. | 504/158 |
| 4,092,432 A * | 5/1978 | Bjorklund et al. | 514/634 |
| 4,253,971 A * | 3/1981 | MacLeod et al. | 504/122 |
| 4,558,159 A * | 12/1985 | McCoy et al. | 564/233 |
| 4,758,595 A | 7/1988 | Ogunbiyi et al. | |
| 4,814,334 A | 3/1989 | Salkin | |
| 4,836,986 A | 6/1989 | Ogunbiyi et al. | |
| 4,891,423 A * | 1/1990 | Stockel | 528/422 |
| 4,952,704 A * | 8/1990 | Merianos | 548/519 |
| 5,000,867 A | 3/1991 | Heinhuis-Walther et al. | |
| 5,141,803 A * | 8/1992 | Pregozen | 428/288 |
| 5,449,658 A * | 9/1995 | Unhoch et al. | 504/151 |
| 5,668,084 A * | 9/1997 | Unhoch et al. | 504/158 |
| 5,670,160 A | 9/1997 | Eggensperger et al. | |
| 5,830,546 A * | 11/1998 | Ehret et al. | 428/36.1 |
| 5,990,174 A | 11/1999 | Henry | |
| 6,121,327 A * | 9/2000 | Tsuzuki et al. | 514/642 |
| 6,214,596 B1 * | 4/2001 | Asgharian et al. | 435/188 |

FOREIGN PATENT DOCUMENTS

| | | |
|---|---|---|
| EP | 0099209 | 1/1984 |
| EP | 0185970 | 7/1986 |
| JP | 2000026894 | 1/2000 |

OTHER PUBLICATIONS

STN File Registry Solubility Data for propyleneglycol 2001 American Chemical Society.*

* cited by examiner

*Primary Examiner*—Sreeni Padmanabhan  
*Assistant Examiner*—Gina C. Yu  
(74) *Attorney, Agent, or Firm*—Pillsbury Winthrop Shaw Pittman LLP

(57) ABSTRACT

A stable aqueous concentrate comprising a polymeric biguanide, a chelating agent and a water-miscible organic solvent for controlling the growth of algae, fungi and pathogenic organisms in water.

26 Claims, No Drawings

COMPOSITION FOR CONTROLLING THE GROWTH OF ALGAE, FUNGI AND PATHOGENIC ORGANISMS IN WATER

FIELD OF INVENTION

The present invention relates to compositions for controlling the growth of algae, fungi and pathogenic organisms in water, especially recreational water such as swimming pools and spas. More particularly the invention relates to aqueous concentrates comprising a polymeric biguanide or a salt thereof, ethylenediaminetetraacetic acid or a salt thereof and a water-miscible organic solvent.

BACKGROUND OF THE INVENTION

The water in swimming pools and spas is constantly re-circulated, and fresh water is normally added only to maintain the desired volume. Although the water is usually filtered continuously to keep it free from suspended matter, it is constantly exposed to infection by pathogenic organisms (bacteria), algae and fungi. Treatment is therefore necessary to control these infections and infestations for reasons of hygiene and appearance.

U.S. Pat. No. 4,014,676 describes the use of poly(hexamethylene biguanide) (PHMB) for controlling algae in swimming pools, and PHMB is commercially available from Avecia, Inc. as a chlorine-free swimming pool sanitizer and algistat under the trademark BAQUACIL. However, while PHMB is a good product for killing pathogenic organisms (a bactericide) in swimming pools and spas at levels of 6–10 ppm, it is generally only algi-static and fungistatic at these levels. Thus the use of PHMB alone to treat swimming pool and spa water will not prevent algal and fungal infestations in the pool.

Swimming pool or spa water can contain a variety of metal ions such as copper, iron and manganese and mineral ions such as calcium. These ions, if present in the water, can reduce the effectiveness of the sanitizer and lead to the development of cosmetically unappealing stains. Chelating agents, such as ethylenediaminetetraacetic acid (EDTA) are often added to water in swimming pools and spas to protect the surfaces and components from being stained by mineral and metal ions and their oxides, hydroxides, carbonates, phosphate, or silicates.

U.S. Pat. No. 5,449,658 discloses that EDTA potentiates PHMB and that a composition comprising EDTA and PHMB provides protection against bacterial, fungal and algal infestations in water. The patent also suggests adding the PHMB and EDTA to the water as a solid or liquid concentrate so as to provide the desired level of PHMB and EDTA in the water. The patent suggests an aqueous concentrate containing from 5–20 weight % PHMB and about 0.5–10 weight % EDTA.

However, we have found that when polymeric biguanides, such as PHMB, are formulated with EDTA in water at the concentrations suggested in U.S. Pat. No. 5,449,648, the resulting formulation is not stable, particularly when the formulation is stored under adverse conditions such as extremes of temperature or extended storage times. We have found that such solutions become cloudy and often form precipitates. The precipitation of the EDTA and/or PHMB from the concentrate results in the incorrect dosage of one or both of these components in the formulation when it is added to the water to be treated, thus reducing the microbiological protection provided by the composition.

There is therefore a need for a stable liquid concentrate of a polymeric biguanide and a chelating agent such as EDTA.

SUMMARY OF THE INVENTION

According to the present invention there is provided a composition comprising:
  (a) from 5 to 25 parts of a polymeric biguanide or a salt thereof;
  (b) at least 3 parts of a chelating agent;
  (c) at least 1 part of a water-miscible organic solvent; and
  (d) up to 91 parts water;

wherein all parts are by weight and the parts (a)+(b)+(c)+(d)=100.

DETAILED DESCRIPTION OF THE INVENTION

The composition preferably comprises:
  from 10 to 25, more preferably from 15 to 23, especially from 18 to 22, and more especially from 19 to 21 parts of the polymeric biguanide or salt thereof (component (a));
  from 3 to 30 more preferably from 5 to 25, especially from 10 to 16, and more especially from 13 to 15 parts of the chelating agent (component (b));
  from 1 to 40, more preferably 5 to 35 and especially 13.5 to 30 parts of water-miscible organic solvent (component (c)); and
  from 5 to 86, more preferably from 17 to 75 and especially from 32 to 58.5 parts water (component (d));

wherein all parts are by weight and the parts (a)+(b)+(c)+(d)=100.

Polymeric Biguanide (Component (a))

The polymeric biguanide contains at least two biguanide units of Formula (1):

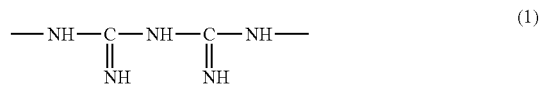

(1)

which are linked by a bridging group which contains at least one methylene group. Preferably the bridging group includes a polymethylene chain which is optionally substituted by hetero atoms such as oxygen, sulphur or nitrogen. The bridging group may include one or more cyclic nuclei which may be saturated or unsaturated. Preferably, the bridging group is such that there are at least three, and especially at least four, carbon atoms directly interposed between two adjacent biguanide units of Formula (1). Preferably, there are not greater than 10 and especially not greater than eight carbon atoms interposed between two adjacent biguanide units of Formula (1).

The polymeric biguanide may be terminated by any suitable group which may be a hydrocarbyl or substituted hydrocarbyl group or an amine or a cyanoguanidine group of the formula:

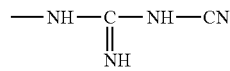

When the terminating group is a hydrocarbyl group, it is preferably alkyl, cycloalkyl or aralkyl.

When the terminating group is a substituted hydrocarbyl group, the substituent may be any substituent that does not exhibit undesirable adverse effects on the microbiological properties of the polymeric biguanide. Examples of such substituents or substituted hydrocarbyl groups are aryloxy, alkoxy, acyl, acyloxy, halogen and nitrile.

When the polymeric biguanide contains two biguanide groups of Formula (1), the two biguanide groups are preferably linked through a polymethylene group, especially a hexamethylene group and the biguanide is a bisbiguanide.

The terminating groups in such bisbiguanides are preferably $C_{1-10}$-alkyl which may be linear or branched and optionally substituted aryl, especially optionally substituted phenyl. Examples of such terminating groups are 2-ethyl hexyl and 4-chloro phenyl. Specific examples of such bisbiguanides are compounds represented by Formula (2) and (3) in the free base form:

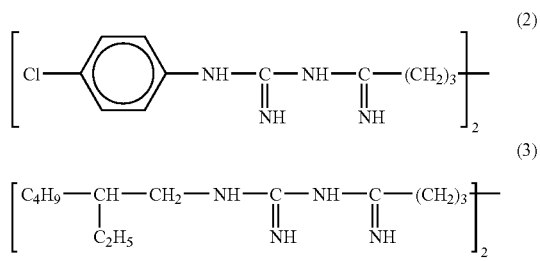

The polymeric biguanide preferably contains more than two biguanide units of Formula (1) and is preferably a linear polymeric biguanide which has a recurring polymeric chain represented by Formula (4) or a salt thereof:

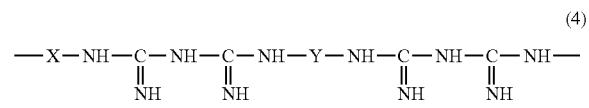

wherein X and Y represent bridging groups in which together the total number of carbon atoms directly interposed between the pairs of nitrogen atoms linked by X and Y is more than 9 and less than 17.

The bridging groups X and Y preferably consists of polymethylene chains, optionally interrupted by hetero atoms, for example, oxygen, sulphur or nitrogen. X and Y may also incorporate cyclic nuclei which may be saturated or unsaturated, in which case the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

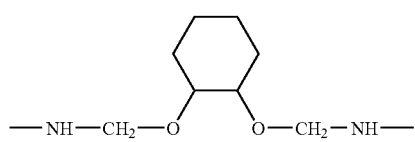

is 4 and not 8.

The linear polymeric biguanides having a recurring polymer unit of Formula (4) are typically obtained as mixtures of polymers in which the polymer chains are of different lengths. Preferably, the number of individual biguanide units of formulae:

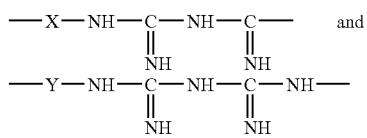

is, together, from 3 to about 80.

The preferred linear polymeric biguanide is a mixture of polymer chains in which the individual polymer chains, excluding the terminating groups, are of the Formula (5) or a salt thereof:

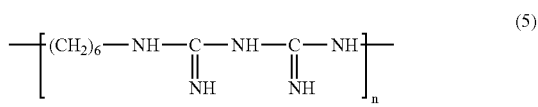

wherein n is from 4 to 40 and especially from 4 to 15. It is especially preferred that the average value of n is about 12. Preferably, the average molecular weight of the polymer in the free base form is from 1100 to 3300.

The linear polymeric biguanides may be prepared by the reaction of a bisdicyandiamide having the formula:

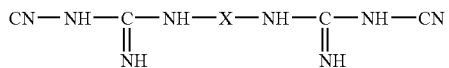

with a diamine $H_2N$—Y—$NH_2$, wherein X and Y have the meanings defined above or by reaction between a diamine salt or dicyanimide having the formula:

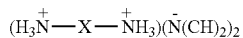

with a diamine $H_2N$—Y—$NH_2$ wherein X and Y have the meanings defined above. These methods of preparation are described in UK specifications numbers 702,268 and 1,152,243 respectively, and any of the polymeric biguanides described therein may be used.

As noted hereinbefore, the polymer chains of the linear polymeric biguanides may be terminated either by an amino group or by a cyanoguanidine group:

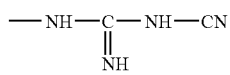

This cyanoguanidine group can hydrolyse during preparation of the linear polymeric biguanide yielding a guanidine end group. The terminating groups may be the same or different on each polymer chain.

A small proportion of a primary amine R—NH$_2$, where R represents an alkyl group containing from 1 to 18 carbon atoms, may be included with the diamine H$_2$N—Y—NH$_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used.

The polymeric biguanides readily form salts with both inorganic and organic acids. Preferred salts of the polymeric biguanide are water-soluble. When the polymeric biguanide is represented by a compound of Formula (2) in the free base form, a preferred water soluble salt is the digluconate. When the polymeric biguanide is represented by a compound of Formula (3) in the free base form, a preferred water soluble salt is the diacetate and where the much preferred polymeric biguanide is a mixture of linear polymers represented by Formula (5) in the free base form, the preferred salt is the hydrochloride.

It is especially preferred that the polymeric biguanide is a mixture of linear polymers, the individual polymer chains of which, excluding the terminating groups, are represented by Formula (5) in the hydrochloride salt form. This is commercially available from Avecia Inc. under trademark BAQUACIL®.

Chelating Agent (Component (b))

Preferred chelating agents are water-soluble compounds capable of forming a complex with metal ions which may be present in a swimming pool or spa, for example copper, iron, manganese and especially calcium. Examples of water-soluble chelating agents include aminocarboxylic acids, such as nitrilotriacetic acid; polyaminocarboxylic acids, such as ethylenediaminetetraacetic acid (hereinafter referred to as "EDTA"), ethyleneglycol tetraacetic acid, trans-1,2-cyclohexenediaminetetraacetic acid, di-2,3-butylenediamine tetraacetic acid, di-1,2-butylenediaminetetraacetic acid, di-1,2-diaminepropanetetraacetic acid, N-(2-hydroxyethyl)-ethylenediaminetriacetic acid, and 1,2-di-phenylethylenedi-aminetetraacetic acid; hydroxycarboxylic acids, such as citric acid, and gluconic acid; aminoalcohols, such as triethanolamine; phosphonic acids such as hydroxyethylidene-diphosphonic acid and ethylenedinitrilotetrakis(methane phosphonic acid); and polyphosphates such as hexametaphosphate and derivatives thereof. The chelating agent may be used in free acid/base form or in the form a salt.

It is especially preferred that the chelating agent is EDTA or a salt thereof. Preferred salts of EDTA are the Na salt and K salt, more preferably the disodium or trisodium and especially the tetrasodium salts, because these minimise pH variations when added to swimming pool or spa water.

Water-Miscible Organic Solvent (Component (c))

Preferred water-miscible organic solvents include C$_{1-6}$-alkanols (especially C$_{1-4}$-alkanols), for example methanol, ethanol, n-propanol, isopropanol, n-butanol, sec-butanol, tert-butanol, n-pentenol, cyclopentanol and cyclohexanol; linear amides, preferably dimethylformamide or dimethylacetamide; alkanolamides, for example lactamide, lactamidopropyltrimethylammonium chloride, acetamide and acetamidomonoethanolamine; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, 1,3-butylene glycol, pentylene glycol, hexylene glycol and thiodiglycol and oligo- and poly-alkyleneglycols, preferably diethylene glycol, triethylene glycol, polyethylene glycol, dipropylene glycol, tripropylene glycol and polypropylene glycol; triols, preferably glycerol and 1,2,6-hexanetriol; mono-C$_{1-4}$-alkyl ethers of diols, preferably mono-C$_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol, propyleneglycol butyl ether and 1-propoxy-2-propanol.

It is especially preferred that the water-miscible organic solvent is a glycol with 2 to 6 carbon atoms, a poly-alkylene glycol with 4 to 9 carbon atoms or a mono C$_{1-4}$-alkyl ether of a glycol with 3 to 13 carbon atoms. The most preferred water-miscible organic solvent is propylene glycol because of its low toxicity to humans and good aqueous solubility.

The composition preferably has a pH in the range of from 8.0 to 11.0, more preferably from 8.0 to 10.0 and especially from 8.1 to 8.5. The pH of the composition may be adjusted using any suitable agent, for example a mineral acid such as hydrochloric acid.

Preferably the composition has a viscosity at 25° C. of from 2 to 500, more preferably from 50 to 350 and especially from 65 to 300 cps.

In a first preferred embodiment of the present invention the composition comprises:

(a) from 5 to 25 parts of a polymeric biguanide or a salt thereof;
(b) from 3 to 30 parts of EDTA or a salt thereof;
(c) from 20 to 35 parts of one or more water-miscible organic solvent(s) selected from a glycol with 2 to 6 carbon atoms, a poly-alkylene glycol with 4 to 9 carbon atoms and a mono C$_{1-4}$-alkyl ether of a glycol with 3 to 13 carbon atoms (more preferably ethylene glycol or propylene glycol); and
(d) 10 to 72 parts water;

wherein all parts are by weight and the parts (a)+(b)+(c)+(d)=100.

It is especially preferred that in this first preferred embodiment that component (a) is a linear polymeric biguanide which is a mixture of polymer chains represented by the hereinbefore defined Formula (5) or a salt thereof and that component (c) is propylene glycol.

In a second preferred embodiment the composition comprises:

(a) from 5 to 25 parts of a polymeric biguanide or a salt thereof;
(b) from 5 to 20 parts of EDTA or a salt thereof;
(c) from 20 to 35 parts of one or more water-miscible organic solvent(s) selected from a glycol with 2 to 6 carbon atoms, a poly-alkylene glycol with 4 to 9 carbon atoms and a mono C$_{1-4}$-alkyl ether of a glycol wherein the ether has 3 to 13 carbon atoms (more preferably ethylene glycol or propylene glycol); and
(d) 20 to 70 parts water;

wherein all parts are by weight and the parts (a)+(b)+(c)+(d)=100; and the weight ratio of component (c):component (b) is from 1.6 to 3.0:1.0, more preferably from 1.65 to 2.60:1.00 and especially from 1.70 to 2.00:1.00.

We have found that at these preferred ratios of component (c):component (b) the compositions are particularly stable under conditions of variable temperature, especially conditions of freeze-thaw. Particularly stable compositions are obtained when component (c) is propylene glycol and the weight ratio of propylene glycol:EDTA is from 1.70 to 2.00:1.00.

The freeze-thaw stability of the composition according to this second preferred embodiment is further improved if the pH of the composition is from 8.0 to 9.9, more preferably 8.1 to 8.5.

The composition may contain other components for example a colorant, fragrances, pH adjusting agents, viscosity modifiers.

The compositions according to the present invention may be prepared by mixing the components (a) to (d) to give a solution. Preferably the components are mixed at an elevated temperature, more preferably at a temperature of from 40 to 80° C. and especially at from 40 to 60° C. We have found that the use of an elevated temperature during mixing reduces the mixing time required to obtain the desired solution. The composition may be filtered after mixing to remove any residual particulate matter which may be present.

The liquid compositions of the invention are used to prevent or control the growth of fungi, algae and pathogenic organisms in water. The composition is added to the water in an amount sufficient to give a micro-biological effect in the water.

Preferably the composition is used to treat recreational or industrial water, more preferably a cooling water system and especially a swimming pool or a spa.

The composition is preferably added to the water in a quantity sufficient to give a concentration by weight in the water of from 3 to 14 ppm, more preferably from 6 to 10 ppm of the polymeric biguanide or salt thereof and from 1.5 to 11 ppm more preferably from 1.5 to 6 ppm of the EDTA or salt thereof. However, when the composition is added to water which contains a high biological loading it may be necessary to add an extra amount of the composition to bring the algae, fungi and pathogenic organisms under control.

In general, after initial addition of the composition to the water at the desired concentration further composition may be added periodically to ensure continued protection against bacteria, fungi and algae in the water. The frequency of additional dosage of the composition will be determined by the particular use of the water and whether any additional biological load is added to the water over time. Except in cases of particularly heavy use or extra biological loading, it is generally not necessary to add further doses of the composition more frequently than every two weeks.

The biological activity of the composition may be further enhanced by adding a backup agent comprising a peroxy salt in addition to the composition to the water as described in U.S. Pat. No. 5,449,658, col. 4, lines 19 to 34. Preferred peroxy salt are those which are inactive towards polymeric biguanide. Examples of preferred peroxy salts include sodium persulphate, perborate salts (especially sodium perborate) or peracetate salts. The addition of the composition according to the invention together with a peroxy salt is particularly effective as a shock treatment to challenge and bring under control initially high levels of bacteria, algae and/or fungi present in the water.

The invention is further illustrated by the following examples wherein all percentages are by weight.

EXAMPLE 1

A 1 liter beaker was charged with a 50% aqueous solution PHMB in the hydrochloride salt form (400 g). The PHMB was heated to 50° C. Then 220 grams of propylene glycol was added. The mixture was stirred and heated to 50° C. The tetrasodium salt of EDTA (160 g) was added to the beaker and the mixture was stirred until the EDTA had dissolved. The pH of the mixture was adjusted to about 8.3 and then the dilution water, dye and fragrance were added. A clear water-like solution was obtained.

EXAMPLE 2

A one liter beaker was charged with a 32% aqueous solution of PHMB in the hydrochloride salt form (301 g) and heated to 50° C. Lactamidopropyltrimethylammonium chloride (100 g commercially available from Croda as "Incromectant LMEA") was then added to the beaker and the mixture was stirred. The mixture was heated to 50° C. and EDTA tetraammonium salt (106 g) was added to the beaker was stirred. The pH was about 9.0. A clear solution was obtained.

EXAMPLE 3

A one liter beaker was charged with a 32% aqueous solution of PHMB in the hydrochloride salt form (301 g) and heated to 50° C. Acetamidomonoethanolamine (100 g, commercially available from Croda as "Incromectant MEA") was added to the beaker and the mixture was stirred. The mixture was heated to 50° C. and EDTA tetraammonium salt (106 g) was added to the beaker was stirred. The pH was about 9.0. A clear solution was obtained.

EXAMPLE 4

Experimental Unit Manufacture

A 350–500 gallon reactor was charged with a 40% aqueous solution of PHMB (262.5 kg). The PHMB was heated to 50° C. The vessel was then charged with of USP propylene glycol (110 kilograms) and mixed. The mixture was also heated to 50° C. The vessel was then charged with EDTA (80 kg) and stirred until all of the EDTA was dissolved. The pH was then adjusted to between 8.1 and 8.3 using an 18% hydrochloric acid solution. Then enough water was added to bring the total weight to 500 kg. A clear water-like solution was obtained.

EXAMPLE 5

Low Temperature Stability

Each of the samples shown in Table 1 were stored at −20° C. for 24 hours, removed and allowed to warm to room temperature, visual observations were recorded. This was repeated two additional times. The desired appearance was no worse than a slight haze.

Table 1

| BATCH | PHMB (%) | EDTA (%) | PG (%) | pH | Visual Observations | | |
|---|---|---|---|---|---|---|---|
| | | | | | −20 Cycle 1 | −20 Cycle 2 | −20 Cycle 3 |
| 1 | 20 | 10 | 2.5 | 10 | Cloudy | Cloudy | Cloudy |
| 2 | 20 | 10 | 5 | 9.83 | Cloudy | Cloudy | Cloudy |
| 3 | 20 | 10 | 10 | 9.91 | Cloudy | Cloudy | Cloudy |

-continued

| BATCH | PHMB (%) | EDTA (%) | PG (%) | pH | Visual Observations | | |
|---|---|---|---|---|---|---|---|
| | | | | | −20 Cycle 1 | −20 Cycle 2 | −20 Cycle 3 |
| 4 | 20 | 10 | 12 | 9.8 | Cloudy | Cloudy | Cloudy |
| 5 | 20 | 10 | 20 | 9.79 | Clear | Clear | Clear |
| 6 | 20 | 20 | 15 | 9.87 | Cloudy | Cloudy | Cloudy |
| 7 | 20 | 20 | 20 | 10.1 | Cloudy | Cloudy | Cloudy |
| 8 | 16 | 14 | 24 | 9.6 | Clear | Clear | Slight Haze |
| 9 | 16 | 14 | 24 | 8.3 | Clear | Clear | Clear |
| 10 | 16 | 14 | 26 | 8.3 | Clear | Clear | Clear |
| 11 | 16 | 14 | 28 | 8.28 | Clear | Clear | Clear |
| 12 | 16 | 16 | 26 | 8.31 | Clear | Clear | Slight Haze |
| 13 | 16 | 16 | 28 | 8.3 | Clear | Clear | Slight Haze |
| 14 | 20 | 14 | 25 | 8.26 | Slight Haze | Cloudy | Cloudy |
| 15 | 20 | 14 | 26 | 8.25 | Clear | Clear | Cloudy |
| 16 | 20 | 14 | 27 | 8.25 | Clear | Clear | Slight Haze |
| 17 | 20 | 16 | 25 | 8.27 | Slight Haze | Cloudy | Cloudy |
| 18 | 20 | 16 | 26 | 8.26 | Clear | Slight Haze | Cloudy |
| 19 | 20 | 16 | 27 | 8.25 | Clear | Slight Haze | Cloudy |
| 20 | 20 | 16 | 28 | 9.02 | Clear | Clear | Slight Haze |

The invention claimed is:

1. A freeze-thaw stable aqueous polymeric biguanide composition comprising:
   (a) from 5 to 25 parts of a polymeric biguanide or salt thereof;
   (b) at least 3 parts of a chelating agent;
   (c) at least 1 part of propylene glycol; and
   (d) up to 91 parts water;
wherein all parts are by weight and the parts (a)+(b)+(c)+(d)≈100, whereby said composition has improved resistance against formation of cloudiness when the composition is subjected to freeze-thaw conditions.

2. A composition according to claim 1 comprising:
   from 10 to 25 parts of the polymeric biguanide or salt thereof;
   from 3 to 30 parts of the chelating agent;
   from 1 to 40 parts of propylene glycol; and
   from 5 to 86 parts water;
wherein all parts are by weight and the parts (a)+(b)+(c)+(d)=100.

3. A composition according to claim 1 wherein the polymeric biguanide comprises at least two biguanide units of Formula (1):

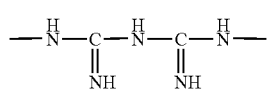

Formula (1)

which are linked by a bridging group which contains at least one methylene group.

4. A composition according to claim 1 wherein the polymeric biguanide comprises a linear polymeric biguanide which as a recurring polymeric chain represented by Formula (4) or a salt thereof:

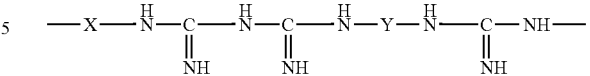

Formula (4)

wherein X and Y represent bridging groups in which together the total number of carbon atoms directly interposed between the pairs of nitrogen atoms linked by X and Y is more than 9 and less than 17.

5. A composition according to claim 1 wherein the chelating agent is ethylenediaminetetraacetic acid or a salt thereof.

6. A composition according to claim 1 where the pH is in the range of from 8.0 to 11.0.

7. A freeze-thaw stable aqueous polymeric biguanide composition comprising:
   (a) from 5 to 25 parts of a polymeric biguanide or salt thereof;
   (b) from 3 to 30 parts of EDTA or a salt thereof;
   (c) from 20 to 35 parts of propylene glycol; and
   (d) 10 to 72 parts water;
wherein all parts are by weight and the parts (a)+(b)+(c)+(d)=100, whereby said composition has improved resistance against formation of cloudiness when the composition is subjected to freeze-thaw conditions.

8. A freeze-thaw stable aqueous polymeric biguanide composition comprising:
   (a) from 5 to 25 parts of a polymeric biguanide or salt thereof;
   (b) from 5 to 20 parts of EDTA or a salt thereof;
   (c) from 20 to 35 parts of propylene glycol; and
   (d) 20 to 72 parts water;
wherein all parts are by weight and the parts (a)+(b)+(c)+(d)=100, whereby said composition has improved resistance against formation of cloudiness when the composition is subjected to freeze-thaw conditions.

9. A composition according to claim 1, wherein the polymeric biguanide is a mixture of polymer chains in which the individual polymer chains, excluding the terminating groups, are of the Formula (5) or a salt thereof:

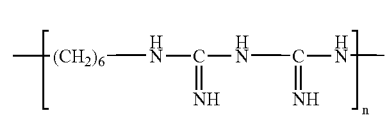

Formula (5)

wherein n is from 4 to 40.

10. A composition according to claim 9, wherein n is from 4 to 15.

11. A method for preparing a stable aqueous polymeric biguanide composition comprising: mixing the following ingredients to form a solution of the polymeric biguanide:
   (a) from 5 to 25 parts of a polymeric biguanide or salt thereof;
   (b) at least 3 parts of a chelating agent;
   (c) at least 1 part of a propylene glycol; and
   (d) up to 91 parts water;
wherein all parts are by weight and the parts (a)+(b)+(c)+(d)=100, whereby the resulting composition has improved resistance against becoming cloudy when subject to freeze-thaw conditions.

12. A method according to claim 11, wherein the ingredients are mixed at a temperature in the range of 40° C. to 80° C.

13. A method accoarding to claim 11, further comprising filtering the resulting composition to remove particulate matter.

14. A method according to claim 11, which comprises mixing the ingredients (a), (b), (c) and (d) in the following amounts, by weight,
(a) 5 to 25 parts
(b) 3 to 30 parts
(c) 20 to 35 parts
(d) 10 to 72 parts.

15. A method according to claim 11, which comprises mixing the ingredients (a), (b), (c) and (d) in the following amounts, by weight,
(a) 5 to 25 parts
(b) 5 to 20 parts
(c) 20 to 35 parts
(d) 20 to 70 parts.

16. A method according to claim 11, wherein the chelating agent (b) is ethylenediamine tetraacetic acid or salt thereof.

17. A method according to claim 16, which comprises mixing the ingredients (a), (b), (c) and (d) in the following amount, by weight,
(a) 5 to 25 parts
(b) 5 to 20 parts
(c) 20 to 35 parts
(d) 20 to 70 parts.

18. A method according to claim 17, which comprises mixing (b) and (c) in a ratio, by weight, of (b):(c) from 1.6 to 3.0:1.00.

19. A method according to claim 17, which comprises mixing (b) and (c) in a ratio, by weight, of (b):(c) from 1.65 to 2.50:1.00.

20. A method according to claim 17, which comprises mixing (b) and (c) in a ratio, by weight, of (b):(c) from 1.70 to 2.0:1.00.

21. A method according to claim 11, wherein (b) is ethylenediamine tetraacetic acid or salt thereof and wherein the mixing weight ratio of (b):(c) is from 1.70 to 2.00:1.

22. A method according to claim 21, further comprising adjusting the pH of the resulting composition to within the range of from 8.0 to 9.9.

23. A freeze-thaw stable aqueous polymeric biguanide composition prepared according to the method of claim 11.

24. A method for treating recreational or industrial water comprising adding a microbiologically effective amount of the composition according to claim 1 to said recreational or industrial water.

25. A method for treating recreational or industrial water comprising adding a microbiologically effective amount of the composition according to claim 7 to said recreational or industrial water.

26. A method according to claim 25, which comprises adding the composition in amount sufficient to provide from 3 to 14 ppm of polymeric biguanide or salt thereof and from 6 to 10 ppm of chelating agent in the water to the treated.

* * * * *